US010667767B2

(12) United States Patent
Stevens et al.

(10) Patent No.: US 10,667,767 B2
(45) Date of Patent: Jun. 2, 2020

(54) SYSTEMS AND METHODS FOR SELECTING BOWTIE FILTER CONFIGURATION

(71) Applicant: General Electric Company, Schenectady, NY (US)

(72) Inventors: Grant Morey Stevens, Waukesha, WI (US); Dominic Joseph Crotty, Waukesha, WA (US); Roy A. Nilsen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 862 days.

(21) Appl. No.: 14/268,404

(22) Filed: May 2, 2014

(65) Prior Publication Data

US 2015/0313569 A1    Nov. 5, 2015

(51) Int. Cl.
*A61B 6/03* (2006.01)
*A61B 6/00* (2006.01)
(Continued)

(52) U.S. Cl.
CPC .............. *A61B 6/032* (2013.01); *A61B 6/035* (2013.01); *A61B 6/4035* (2013.01); *A61B 6/488* (2013.01);
(Continued)

(58) Field of Classification Search
CPC .. A61B 6/00; A61B 6/03; A61B 6/032; A61B 6/035; A61B 6/04; A61B 6/0407; A61B 6/0457; A61B 6/10; A61B 6/40; A61B 6/4035; A61B 6/405; A61B 6/48; A61B 6/488; A61B 6/54; A61B 6/542; A61B 6/544; A61B 6/545; A61B 6/547; A61B 6/58; A61B 6/582; A61B 6/586; A61B 6/589; A61B 2560/00;
(Continued)

(56) References Cited

U.S. PATENT DOCUMENTS 3,717,768 A    2/1973    Edholm et al.
3,860,817 A    1/1975    Carmean
(Continued)

FOREIGN PATENT DOCUMENTS

JP    2002-102217    9/2002

*Primary Examiner* — Anastasia Midkiff
(74) *Attorney, Agent, or Firm* — The Small Patent Law Group LLC; Dean D. Small

(57) ABSTRACT

An imaging system is provided including a selectable pre-object filter module, a detector, and a processing unit. The selectable pre-object filter module is configured to absorb radiation from the X-ray source to control distribution of X-rays passed to an object to be imaged. The selectable pre-object filter module has plural pre-object filter configurations providing corresponding X-ray distributions, and is selectable between the plural configurations to provide a selected pre-object filter configuration for a scan of the object. The detector is configured to receive X-rays that have passed through the object. The processing unit is operably coupled to the selectable pre-object filter module and the detector, and is configured to identify an anatomy to be imaged, determine a corresponding image quality and radiation dose for each of the plural pre-object filter configurations; and select the selected pre-object filter configuration based upon the determined corresponding image qualities and radiation doses.

22 Claims, 7 Drawing Sheets

(51) Int. Cl.
*A61B 6/04* (2006.01)
*G21K 1/10* (2006.01)

(52) U.S. Cl.
CPC .............. *A61B 6/542* (2013.01); *A61B 6/544* (2013.01); *A61B 6/0457* (2013.01); *A61B 6/4078* (2013.01); *A61B 6/545* (2013.01); *A61B 6/589* (2013.01); *G21K 1/10* (2013.01)

(58) Field of Classification Search
CPC ........ A61B 2560/02; A61B 2560/0223; A61B 2560/0266; A61B 2560/0276; A61B 2560/029; A61B 2576/00; A61N 2005/1095; G01N 2021/6471; G01N 2201/06; G01N 2201/068; G01N 2223/30; G01N 2223/303; G01N 2223/3032; G01N 2223/306; G01N 2223/313; G01N 2223/32; G01N 2223/40; G01N 2223/419; G02B 5/00; G02B 5/02; G02B 5/0273; G02B 5/0294; G02B 5/20; G02B 5/201; G02B 5/206; G02B 5/22; G02B 7/00; G02B 7/003; G02B 7/005; G02B 7/006; G02B 26/00; G02B 26/02; G02B 26/023; G02B 26/10; G02B 27/00; G02B 27/09; G02B 27/0938; G02B 27/0988; G02B 27/62; G02F 1/00; G06F 19/3406; G21K 1/00; G21K 1/02; G21K 1/025; G21K 1/04; G21K 1/043; H01J 35/00; H01J 35/02; H01J 35/025; H01J 37/00; H01J 37/02; H01J 37/023; H01J 37/04; H01J 37/20; H01J 37/22; H01J 37/30; H01J 37/3002; H01J 37/30; H01J 37/302; H01J 37/3023; H01J 37/304; H01J 37/3045; H01J 99/00; H01J 2235/00; H01J 2237/00; H01J 2237/248; H01J 2237/2482; H05G 1/00; H05G 1/02; H05G 1/08; H05G 1/26; H05G 1/30
See application file for complete search history.

(56) References Cited

U.S. PATENT DOCUMENTS

| | | |
|---|---|---|
| 4,288,695 A | 9/1981 | Walters et al. |
| 4,868,843 A | 9/1989 | Nunan |
| 4,975,933 A | 12/1990 | Hampel |
| 5,054,048 A | 10/1991 | Wang |
| 5,148,465 A | 9/1992 | Mulder et al. |
| 5,400,379 A | 3/1995 | Pioh et al. |
| 5,430,783 A | 7/1995 | Hu et al. |
| 5,454,023 A | 9/1995 | Asikainen |
| 5,644,614 A | 7/1997 | Toth et al. |
| 5,828,719 A | 10/1998 | He |
| 5,881,127 A | 3/1999 | Molloi et al. |
| 6,307,918 B1 | 10/2001 | Toth et al. |
| 6,325,539 B1 | 12/2001 | Bromberg et al. |
| 6,501,828 B1 | 12/2002 | Popescu |
| 6,529,575 B1 | 3/2003 | Hsieh |
| 6,618,466 B1 | 9/2003 | Ning |
| 6,647,095 B2 | 11/2003 | Hsieh |
| 7,076,029 B2* | 7/2006 | Toth ........................ A61B 6/032 378/158 |
| 7,082,189 B2 | 7/2006 | Yahata et al. |
| 7,515,689 B2* | 4/2009 | Baba .................... A61B 6/4035 378/156 |
| 2001/0050974 A1* | 12/2001 | Schmitz ................. A61B 6/032 378/159 |
| 2005/0089135 A1* | 4/2005 | Toth ........................ A61B 6/032 378/16 |
| 2005/0089136 A1* | 4/2005 | Toth ........................ A61B 6/032 378/16 |
| 2011/0261926 A1* | 10/2011 | Hangartner ............ A61B 6/032 378/19 |
| 2012/0002782 A1* | 1/2012 | Yoshida ................. A61B 6/032 378/16 |
| 2012/0155609 A1* | 6/2012 | Lemminger ........... A61B 6/032 378/62 |
| 2013/0142304 A1* | 6/2013 | Shiraishi ................ G01N 23/02 378/51 |
| 2013/0182820 A1 | 7/2013 | Proksa |
| 2014/0112441 A1* | 4/2014 | Becker ................... A61B 6/032 378/62 |

\* cited by examiner

SYSTEMS AND METHODS FOR SELECTING BOWTIE FILTER CONFIGURATION

BACKGROUND OF THE INVENTION

The subject matter disclosed herein relates generally to systems and methods for computed tomography (CT) imaging, and for selection of bowtie filtration configuration and/or determination of attenuation of an object to be imaged.

In CT imaging, an X-ray source may be rotated around an object to obtain imaging information. A bowtie filter may be interposed between the X-ray source and the object to be imaged, with the bowtie filter configured to absorb radiation (e.g., from a fan-shaped X-ray beam) to control the distribution of radiation received by the object, for example across a width of the object. A collimator may be used in conjunction with the bowtie filter to direct radiation from the source to the object to be imaged, and to limit radiation directed to the object to a desired field of view.

Different configurations of bowtie filters may be available. For example, differently sized bowtie filters may be configured for differently sized patients. However, due to the current use of a finite number of filters with a largely variable patient population, selection of the appropriate filter may be difficult for patients that do not clearly fall within a given size category associated with the filters (e.g., a patient on or near a borderline size category). Further still, depending on internal structure of the patient and/or a scanning procedure to be performed, the most appropriate bowtie filter may be from a different size category than may be conventionally associated with the patient. Selection of an appropriate bowtie filter may involve complicated interrelationships between numerous parameters, making manual selection by operators prone to error and/or inefficiency.

Further, even if a bowtie configuration may be determined to satisfy certain criteria, the bowtie configuration may still result in poor image quality and/or dosage levels if the object to be imaged is not positioned properly. For example, conventional systems may make centering an object to be imaged (e.g., patient) difficult to achieve and/or to determine. For example, misunderstanding of system design implications or difficulty of visually determining relative positioning by an operator may result in improper positioning. Additionally or alternatively, centering may not be feasible in some instances (e.g., due to individual patient constraints). Such mis-positioning may lead to sub-optimal patient positioning, and sub-optimal image quality.

Further, attenuation of an object (e.g., the ability of the object to attenuate X-rays from a source during passage of X-rays from the source to a detector) may be determined or estimated, for example, using a scout scan, to control performance of the scan. However, conventional approaches are susceptible to error from variabilities or inconsistencies regarding patient positioning during a scout scan, resulting in inaccurate attenuation estimates and reduced quality and/or convenience of imaging.

BRIEF DESCRIPTION OF THE INVENTION

In one embodiment, an imaging system is provided that includes a selectable pre-object filter module, a detector, and a processing unit. The selectable pre-object filter module is interposed between an X-ray source and an object to be imaged, and is configured to absorb radiation from the X-ray source to control distribution of X-rays passed to the object to be imaged. The selectable pre-object filter module has plural pre-object filter configurations providing corresponding X-ray distributions, and is selectable between the plural configurations to provide a selected pre-object filter configuration of the plural pre-object filter configurations to perform a scan of the object to be imaged. The detector is configured to receive X-rays that have passed through the object to be imaged. The processing unit is operably coupled to the selectable pre-object filter module and the detector, and is configured to identify an anatomy to be imaged, determine a corresponding image quality and radiation dose for each of the plural pre-object filter configurations; and select the selected pre-object filter configuration based upon the determined corresponding image qualities and radiation doses.

In another embodiment, a method is provided (e.g., for selecting a pre-object filter configuration for an object to be imaged). The method includes identifying, with at least one processing unit, an anatomy to be scanned by a computed tomography (CT) imaging system including a selectable pre-object filter module having plural pre-object filter configurations providing corresponding X-ray distributions. The method also includes determining, with the at least one processing unit, a corresponding image quality (e.g., image quality metric) for the plural pre-object filter configurations based on the anatomy identified. Further, the method includes determining, with the at least one processing unit, a corresponding radiation dosage (e.g., radiation dosage metric) for the plural pre-object filter configurations based on the anatomy identified. Also, the method includes selecting, with the at least one processing unit, a selected pre-object filter configuration for performing a scan of the anatomy to be scanned based upon the determined corresponding image qualities and radiation doses.

In another embodiment, a tangible and non-transitory computer readable medium is provided for selecting a pre-object filter configuration for an object to be imaged. The tangible and non-transitory computer readable medium includes one or more computer software modules configured to direct one or more processors to identify, an anatomy to be scanned by a computed tomography (CT) imaging system including a selectable pre-object filter module having plural bowtie configurations providing corresponding X-ray distributions. The one or more computer software modules are also configured to direct the one or more processors to determine a corresponding image quality for the plural pre-object filter configurations based on the anatomy identified. Further, the one or more computer software modules are also configured to direct the one or more processors to determine a corresponding radiation dosage for the plural pre-object filter configurations based on the anatomy identified. Also, the one or more computer software modules are configured to direct the one or more processors to select a selected pre-object filter configuration for performing a scan of the anatomy to be scanned based upon the determined corresponding image qualities and radiation doses.

DETAILED DESCRIPTION OF THE INVENTION

Figure 1:
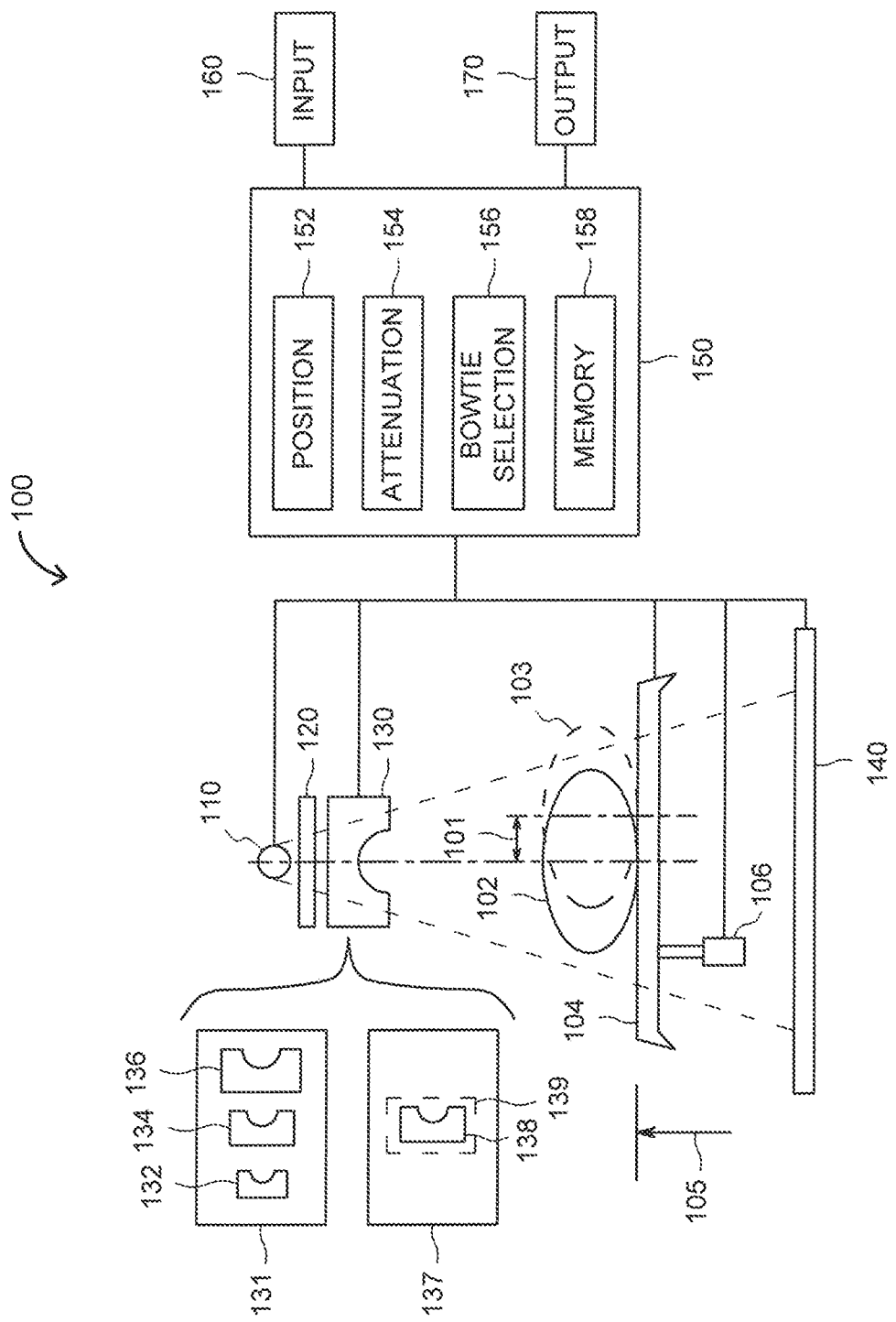
FIG. 1 is a schematic block diagram illustrating an imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for selection of bowtie filter configurations used for imaging (e.g., computed tomography (CT) imaging). Appropriate selection of bowtie filter configuration may provide simplified usability and operation of CT imaging systems, improved imaging quality, and/or improved (e.g., reduced and/or optimized) levels of radiation dose to which a patient being scanned is exposed. In various embodiments, the bowtie configuration may be selected relative to patient size (e.g., attenuation of X-rays through the patient) and positioning (e.g., whether or not the patient is centered in one or more directions). Various embodiments provide for proper centering of a patient to be scanned, improving dosage and noise levels for imaging.

Various embodiments provide for automatic selection of bowtie filter configuration. For example, in some embodiments, the size of anatomy to be scanned may be determined (e.g., using a scout scan). A scout scan may be understood as a preliminary scan performed at generally lower radiation dosages or levels than a scan performed for imaging purposes, with the scout scan (or scans) performed before the imaging scan, for example to help determine the value of one or more operational parameters for use during the imaging scan. As used herein, a scout scan may be understood as a pre-scan. Scout scans, for example, may be performed with an X-ray source and detectors at one or more fixed positions, while an imaging scan may be performed with the X-ray source and detectors rotating about the object (e.g., within a rotating gantry) to provide a more complete (e.g., 360 degree) view of the object. Operational parameters for performing the desired scan may be determined (e.g., obtained via a user input or derived from information provided via a user input).

Further, the relative image quality (e.g., image noise and/or contrast, among others) and/or dosage, based on the selected operational parameters for the scan, may be assessed for different available bowtie filter configurations. Further still, the impact of the bowtie filter selection on other acquisition parameters (e.g., tube current, time required for scan, or the like) may be assessed. An optimal or preferred bowtie configuration may be identified and selected for use in performing a scan to produce an image based on image quality, radiation dosage, and/or impact on other acquisition parameters. Various techniques may be used to identify the optimal or preferred bowtie configuration. For example, an atlas-based approach employing tabulated results for phantoms and/or clinical scans may be employed. Additionally or alternatively, digitally simulated scans may be performed to provide simulated results for various bowtie filter configurations for various combinations of anatomy size, type or purpose of scan, and anatomy position, for example. It may be noted that, in some embodiments, a discrete number of fixed-shape bowtie filters may be selected among, while, alternatively or additionally, in other embodiments, dynamic bowtie filters may be employed, for example with dynamically-changing shapes of one or more bowtie filters identified, selected, and/or implemented.

Additionally or alternatively, patient position determination and/or correction may be performed in various embodiments. For example, an extent or amount of mis-positioning of a patient in one or more dimensions may be determined. An offset from a vertical center may be determined using a scout scan taken from a side of the patient (with the patient facing upward) and/or a scout scan taken from above (or below) a patient, and/or a lateral offset (e.g., left or right) of a center of the patient may be determined using a scout scan taken from above (or below) a patient. If the offset or distance from centered position exceeds a predetermined threshold, a user may be alerted of the mis-positioning. The user may be aided in the correction of the mis-positioning. For example, the user may be provided with instructions to address the mis-positioning (e.g., elevate table or cradle by a given amount, move the patient left or right by a given amount, or the like). In some embodiments a determined mis-positioning may be corrected automatically. For example, the mis-positioning may be addressed autonomously without user involvement, for example with a processing unit determining an amount to move a cradle vertically and moving the cradle the determined amount without user involvement. In other embodiments, the processing unit may determine the amount to move the cradle, and provide the user with a prompt requesting permission to move the cradle the determined amount, with the user provided the option of confirming or denying the requested adjustment.

In some embodiments, the mis-positioning may not be corrected, but instead may be addressed by the selection of acquisition parameters. For example, a modified tube current may be employed for mis-positioned patients. As another example, the bowtie configuration selection may be performed based at least in part on the position of the patient. For example, if a patient is located a relatively large distance off-center, such that a relatively thick or high attenuation portion of a patient is positioned toward an edge of a field of view for which a relatively thin or low attenuation portion would be positioned if centered properly, then a bowtie configuration permitting relatively more radiation toward the edge of the field of view may be selected instead of a bowtie configuration that would have been selected if the patient were properly centered. Similarly, with a relatively lower attenuation portion of the patient disposed along a center of a field of view, a bowtie configuration may be selected providing less radiation to the patient along the center of the field of view than would have been selected if the patient were properly centered. Further still, in some embodiments, particular bow-tie configurations may be provided that provide radiation distributions particularly suited for off-center imaging (e.g., permitting more radiation to pass toward an edge of a field of view and or less radiation to pass relative to a center of a field of view relative to a configuration configured for imaging of properly centered objects). It may be noted that, for embodiments using dynamically adjustable bowtie configurations, the selection of configuration may describe both a bowtie shape and position during a scan.

Various inputs may be received in connection with identifying and/or selecting a bowtie filter configuration. For example, in some embodiments, a user may input scan technique information and/or clinical mode information, and a scout scan may be acquired to provide information on the positioning of the patient. Scan technique information may include, for example, a tube voltage setting (e.g., 120 kV), an image quality metric or index, or the like. Clinical mode information may indicate a clinical mode for the scan, such as a soft-tissue mode, a contrast enhanced mode, an angiogram mode, or a bone mode, among others. An imaging system (e.g., one or more processing units of the imaging system) may then determine patient positioning relative to a system isocenter, and prompt the user to re-position the patient, either manually or through an input to the system. It may be noted that, in some example scenarios, a user may elect not to re-position the patient. The position of the patient after the positioning determination, whether mis-positioned or not, may be understood as a final position or imaging position. The system may then determine the patient attenuation in the final positioning state, and use the patient attenuation in setting one or more acquisition parameters (e.g., tube current) and/or selecting bowtie filter configuration. The system may determine an expected image quality (e.g., contrast and/or noise) and expected radiation dose for each of a group of bowtie filter configurations corresponding to the final positioning state. It may be noted that various metrics may be used to measure image quality or radiation dose.

For example, radiation dose may be measured by one or more of CT dose index (CTDI), size specific dose estimate (SSDE), estimated organ dose, or skin dose, among others. The system may then access, calculate, or otherwise obtain a metric to balance or obtain a trade-off between image quality and radiation dose, and then select a desired or optimal bowtie configuration from among the available configurations based on the image quality and radiation dose (e.g., using the metric that balances or obtains a trade-off between image quality and radiation dose). The determination of the image quality and dose balance or tradeoff may be performed, for example, using an approach that weights the contrast to noise ratio (CNR), overall noise, and CTDI. Other approaches (e.g., using different parameters or image quality or dose metrics) may be employed in various embodiments.

Additionally or alternatively, various embodiments provide for improved determination of attenuation (e.g., attenuation by an object to be imaged such as a human patient or portion thereof). In CT scanning, attenuation determined for an object to be scanned may be used in determining how the scan is performed. For example, automatic exposure control (AEC) mode features may utilize a radiograph or scout scan to localize and estimate the patient attenuation local to the anatomy of interest, and to guide the AEC feature to generate appropriate X-ray exposure to achieve a desired image quality for a given diagnostic task. As patient exposure and radiation dose typically correlate positively with estimated attenuation, accurate and robust patient attenuation estimation may be important in AEC-based workflows.

However, conventional approaches suffer from widely varying attenuation estimates, even for the same patient, depending on scout acquisition techniques, including, for example, varying cradle heights and/or varying azimuths or points of view of the source (e.g., posterior-anterior or anterior-posterior). Radiation dose determined for the same patient and diagnostic task may vary substantially due to changes in cradle height and/or scout azimuth or orientation.

Various embodiments provide methods and/or systems that analyze or assess scout projections in terms of occupied channels (e.g., channels of a detector above a predetermined signal threshold) and cradle height or position (e.g., as determined by a position sensor and/or feedback from a device or system configured to articulate the cradle). For example, the number and/or position of occupied channels may be understood as providing a projection signature, and the projection signature may be compared to archived projection signatures of known historical patient sizes and cradle heights, and/or archived projection signatures of known phantom sizes and shapes at known cradle heights, with the archived projection signature most closely resembling the projection signature obtained via a scout scan used to determine the attenuation of the object to be imaged. For example, the object to be imaged may be estimated as having the same size and shape as the archived size and shape, or may be estimated using the archived size and shape (e.g., estimated based on a normalized or adjusted value using the archived size and shape). Further, the signature of the cradle may be considered, for example the attenuation attributable to the cradle may be used to modify the attenuation estimate to arrive at a final determined attenuation for the object to be imaged.

For example, in some embodiments, a database may be populated with cradle heights and projection signatures (e.g., projection signatures describing occupied detector channels). Based on the known cradle height and scout azimuth for a scout scan, and with the projection signature for the scout scan determined, the database of archived projection signatures may be searched or interrogated to find an archived projection signature (for the corresponding azimuth and/or cradle height) that matches or closely corresponds to the scout scan projection signature. In some embodiments, a cradle-only projection may be subtracted from the patient scout projection signature. The projection signature (with or without the cradle contribution subtracted) may be used to provide a raw patient attenuation estimation, which may be normalized for the number of occupied channels in the scout projection. As the position (e.g., whether or not the object is off-center) is automatically accounted for using the determination of the shape, size, and position, subsequent or additional adjustments for off-center positions need not be made in determining attenuation in various embodiments.

In an example embodiment, a patient may be set up or positioned within an imaging system. Next, a scout scan may be performed. Anatomy to be scanned may then be determined, for example, using the scout scan. Positioning of the patient may next be determined. If the patient is mis-positioned and adjusting is possible, the position of the patient may be adjusted until the patient is properly positioned. If adjusting a mis-positioned patient is not possible, a correction for a pre-object filtering may be determined. If necessary or desired, the determined anatomy may be updated based on the positioning. Next, estimated image quality and radiation dose metrics for various pre-object filtering configurations may be calculated. A particular pre-object filtering configuration to be used in a scan may then be selected based on one or more of the determined anatomy to be scanned, clinical task, patient positioning, image quality, and radiation dose. With the pre-object filtering selected, a scan may be performed using the selected pre-object filtering.

Various embodiments provide improved imaging. For example, a bowtie filter configuration satisfying one or more criteria may be selected. A technical effect of at least one embodiment includes improved imaging, for example by improving selection of bowtie filter configuration to satisfy one or more criteria (e.g., one or more metrics corresponding to image quality and radiation dosage, among others). A technical effect of at least one embodiment includes reducing or eliminating effort required by a user to specify a bowtie filter configuration and/or reducing or eliminating human error in bowtie filter configuration selection. A technical effect of at least one embodiment is to provide optimal or improved levels of radiation dosage for a scan. A technical effect of at least one embodiment is to provide improved identification of position of an object to be scanned (e.g., identification of whether the object is properly centered or mis-positioned). A technical effect of at least one embodiment is to address mis-positioning of a patient in selection of bowtie filter configuration. A technical effect of at least one embodiment includes the automatic addressing of off-centered positioning when determining attenuation.

Figure 2:
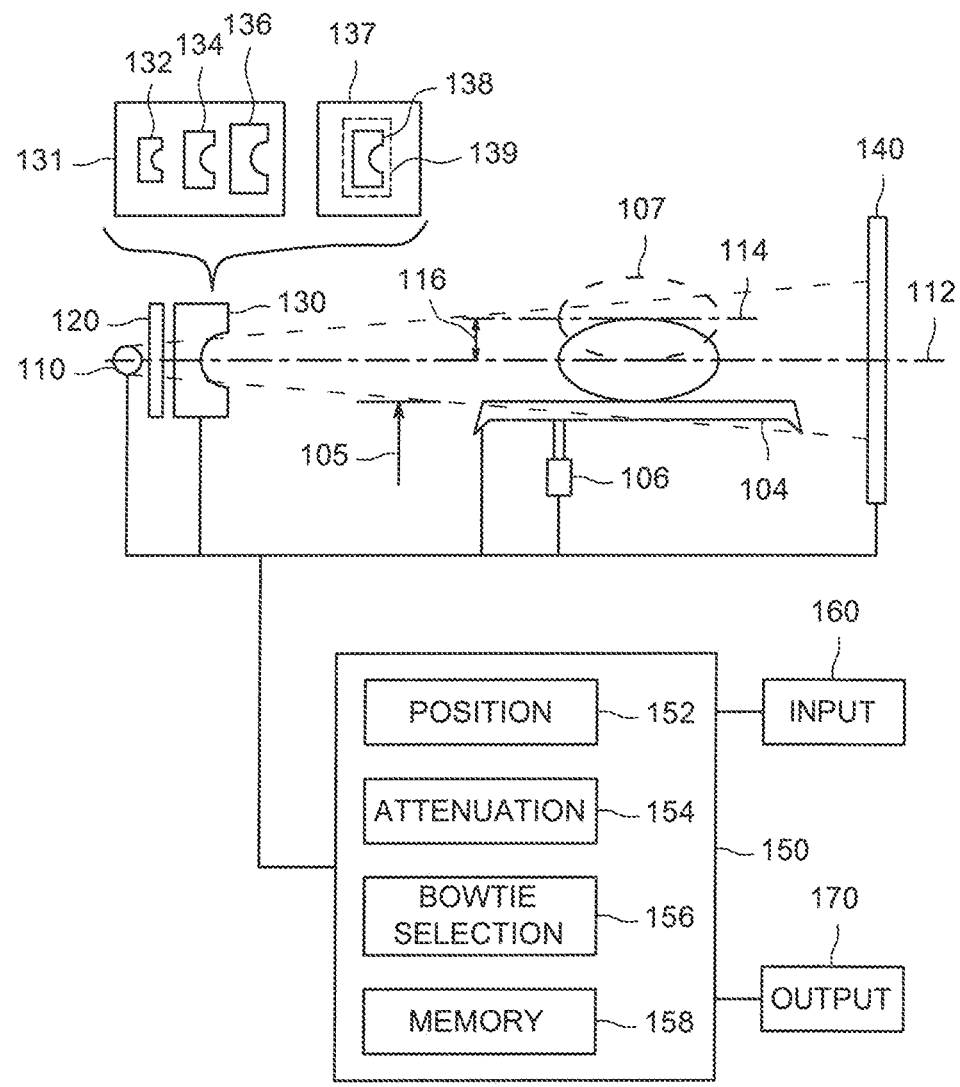
FIG. 2 illustrates an additional view of the imaging system of FIG. 1.

FIGS. 1 and 2 illustrate an imaging system 100 in accordance with an embodiment. The imaging system 100 may be configured, for example, to perform computed tomography (CT) scanning of a subject, such as a human or animal patient. In FIGS. 1 and 2, the imaging system 100 is shown in position to scan an object 102 supported by a cradle 104. As seen in FIG. 1, the depicted imaging system 100 includes an X-ray source 110, a source collimator 120, a detector 140, a processing unit 150, an input unit 160, and a display unit 170. It may be noted that various embodiments may include additional components, or may not include all of the components shown in FIGS. 1 and 2 (for example, various embodiments may provide sub-systems for use with other sub-systems to provide an imaging system). Further, it may be noted that certain aspects of the imaging system 100 shown as separate blocks in FIG. 1 may be incorporated into a single physical entity. For example, the display unit 170 and the input unit 160 may share or be incorporated into a common physical entity (e.g., touchscreen). In the illustrated embodiment, the imaging system 100 is configured to perform CT imaging of an object 102. For example, the object 102 may be a human patient, and the imaging system 100 may perform a CT scan of one or more specified portions of the object 102 (e.g., heart, lungs, head, or region identified by boundaries input by a user, among others).

The X-ray source 110 (along with associated components such as a bowtie filter and source collimator) and the detector 140 may rotate about a central axis of a bore of a gantry (not shown in FIGS. 1 and 2) of the system 100. In FIG. 1, the X-ray source 110 is shown positioned at a top location, and in FIG. 2, the X-ray source 110 is shown positioned in a side location. The object 102 is shown centered in each of FIGS. 1 and 2. The object 102 may be understood as centered when a center of the object (e.g., a geometric center or line corresponding to a maximum attenuation viewed from a given direction) is aligned with a center of the X-ray source 110 (e.g., a geometric center of a field of view provided by the X-ray source 110 through a bowtie filter (e.g., a bowtie filter of the selectable bowtie filter module 130)). A long axis of the object 102 (e.g., a long axis of a patient) may be understood as passing into and out of the page as seen in FIGS. 1 and 2.

In FIG. 1, the system 100 is oriented in an Anterior-Posterior (AP), or top-down azimuth or orientation, with the X-rays passing through an anterior portion of the object 102 first. It should be noted that the X-ray source 110 and detector 140 could be rotated to provide other views. For example, the X-ray source 110 and detector 140 of FIG. 1 could be rotated 180 degrees to provide a posterior-anterior (PA) or bottom-up azimuth or orientation. As another example, the X-ray source 110 and detector 140 of FIG. 1 could be rotated 90 degrees counter-clockwise to provide the orientation depicted in FIG. 2. Returning to FIG. 1, the top-down orientation (or bottom-up orientation) may be used to view the object 102 relative to a lateral center. For example, in FIG. 1, the object 102 is centered laterally (or in a left-right direction), whereas a mis-positioned object 103 is shown in phantom lines offset a distance 101 laterally from the object 103.

In FIG. 2, the lateral orientation may be used to view the object 102 relative to a vertical center. For example, in FIG. 1, the object 102 is centered vertically (or in an up-down or anterior-posterior direction), whereas a mis-positioned object 107 is shown in phantom lines offset a distance 116 vertically from the object 102. It may be noted that attenuation for a human patient may vary most noticeably along an anterior-posterior direction relative to a maximum attenuation line centrally located in the patient, so that vertical alignment may be particularly impactful on efficient use of X-rays for imaging. For example, a bowtie filter may generally be configured to allow passage of a maximum amount or proportion of X-rays along a central line 112 through the bowtie filter (and field of view), and less X-rays along portions disposed toward edges of the field of view. However, if the object 102 were to be off-center vertically (e.g., in the position shown by object 107), the large amount of X-rays passing along a central line of the bowtie filter would pass through an edge or side portion of the object, and a lesser amount of X-rays passing along an edge or side portion of the field of view would pass through the center of the object, or line of maximum attenuation. Accordingly, excessive amounts of X-rays may be received by edge or side portions of the object and overly reduced amounts of X-rays may be received by the central portion of the object, if a conventional bowtie configuration selection approaches are employed for an off-center object.

Generally, X-rays 114 from the X-ray source 110 are guided to the object 102 through the source collimator 120 and selectable bowtie filter module 130. The source collimator 120 is configured to allow X-rays within a desired field of view (FOV) to pass through to the object 102 while blocking other X-rays. The selectable bowtie filter module 130 is configured to absorb radiation from the X-ray source 110 to control distribution of X-rays passed to the object to be imaged. For example, a bowtie filter may be comprised of a metal or other object configured to absorb X-rays. The bowtie filter may have a greater thickness (along the direction of X-ray travel) toward the edges of the bowtie filter and a lesser thickness toward the center of the bowtie filter to allow more X-rays to pass through a central portion of the bowtie filter (and field of view).

The cradle 104 supports the object 102 in a desired position. In the illustrated embodiment, the cradle 104 is translatable in a vertical direction via a cradle actuation mechanism 106. For example, in the illustrated embodiment, the cradle 104 is shown at a cradle height 105. The cradle height 105 may be adjusted by actuating the cradle 104 up or down, as desired, using the cradle actuation mechanism 106. For example, if a patient is positioned with a center below the center of the field of view (or center of bowtie filter, or below the X-ray source) when the system 100 is oriented as seen in FIG. 2, the cradle actuation mechanism 106 may be used to raise the cradle 104 an amount sufficient to align the center of the patient with the center of the field of view. The cradle 104 may also be adjustable axially (e.g., along an axis corresponding to a long axis of a patient) to bring a patient into and out of the bore of the gantry. In connection with the illustrated embodiment, cradle height and cradle height adjustment are discussed. Cradle height may be understood as an example of a cradle dimension or cradle adjustment dimension. It may be noted that, additionally or alternatively, other cradle dimensions may be employed. For example, a cradle may be adjustable laterally additionally or alternatively to having an adjustable height.

In the illustrated embodiment, the selectable bowtie filter module 130 has plural available bowtie filter configurations that provide corresponding X-ray distributions. For example, as discussed in further detail elsewhere herein, an appropriate one of the filter configurations may be selected (e.g., by the processing unit 150) to provide a desired X-ray distribution during a scan for a particular patient, positioning, and/or procedure.

X-rays that pass through the object 102 are attenuated by the object 102 (and cradle 104) and received by the detector 140 (which may have a detector collimator associated therewith), which detects the attenuated X-rays and provides imaging information to the processing unit 150. The processing unit 150 may then reconstruct an image of the scanned portion of the object 102 using the imaging information provided by the detector 140. In the illustrated embodiment, the processing unit 150 is also configured to select a configuration for the selectable bowtie filter module 130 to provide a desired X-ray distribution for use during a scan. For example, as discussed in further detail elsewhere herein, the processing unit 150 may be operably coupled to the selectable bowtie filter module 130 and the detector 140, and configured to identify an anatomy to be imaged, determine a corresponding image quality and radiation dose for plural bowtie configurations, and select a selected bowtie configuration based upon the determined corresponding image qualities and radiation doses for the bowtie configurations. The output unit 170 in the illustrated embodiment may be configured for example, to display an image, such as a scout image obtained prior to collection of imaging information, or, as another example, an image reconstructed using imaging information from the detector 140. The output unit 170 may also be configured to display available and/or selected bowtie filter configurations, additional scan parameters, user options to select scan parameters, or the like. The depicted input unit 160 is configured to obtain input corresponding to imaged scan to be performed, with the processing unit 150 using the input to determine a bowtie filter configuration and/or additional parameters used to perform a scan.

In the illustrated embodiment, the X-ray source 110 is configured to rotate about the object 102 and cradle 104. For example, the X-ray source 110, source collimator 120, selectable bowtie filter module 130 (and/or an individual bowtie filter of the selectable bowtie filter module 130), and detector 140 may be positioned about a gantry bore (not shown in FIGS. 1 and 2 for clarity of illustration) that rotates about the object 102 and cradle 104. As the X-ray source 110 rotates about the object 102 during an imaging scan, X-rays received by the detector 140 during one complete rotation provide a 360 degree view of X-rays that have passed through the object. Other scanning ranges may be used in alternative embodiments. It may also be noted that an individual scout scan may be performed from a single orientation (e.g., top-down or bottom-up). In some embodiments, more than one scout scan may be performed. As one example, a lateral scout scan may be used to determine a vertical position (e.g., centered or not centered vertically), and a top down (or bottom-up) scan may be used to determine a lateral position (e.g., centered or not centered laterally).

The source collimator 120 is configured to control the delivery of X-rays from the X-ray source 110 to the object 102. In the illustrated embodiment, the source collimator 120 is interposed between the X-ray source 110 and the object 102 to be imaged, and adjustable between settings corresponding to different amounts of collimation of rays from the X-ray source 110 allowed to pass to the object 102. In the illustrated embodiment, the source collimator 120 is configured to adjust the size of the collimation length or slab length of radiation to which the object 102 is exposed. The collimation length or slab length in the illustrated embodiment may correspond to a length of the resulting field of view along the axial length of the cradle 104 (e.g., into and out of the page as seen in FIG. 2) at the center of a bore about which the X-ray source 110 rotates. In various embodiments, the source collimator 120 may include adjustable blades to adjust the slab length.

The selectable bowtie filter module 130 has plural available bowtie filter configurations that provide corresponding X-ray distributions. For example, an appropriate one of the filter configurations may be selected (e.g., by the processing unit 150) to provide a desired X-ray distribution during a scan for a particular patient, positioning, and/or procedure. It may be noted that the selectable bowtie filter configurations may be arranged as discrete physical units providing corresponding X-ray distributions and/or as dynamically adjustable or alterable structures that may be adjusted to provide different X-ray distributions. It may be further be noted that bowtie filters provide one example of pre-object filters and that, while bowtie filters are discussed in connection with illustrated embodiments, other embodiments may include one or more different types of pre-object filters that may be selectable or adjustable as discussed herein in connection with bowtie filters. For example, in some embodiments, a flat filter (or flat filter module) may have selectable flat filter configurations that may be selected as discussed herein.

For example, in the illustrated embodiment, the selectable bowtie filter module 130 includes both discrete and individually adjustable bowtie filters. The selectable bowtie filter module 130 includes discrete filter module 131 and adjustable filter module 137.

The discrete filter module 131 includes a first bowtie filter 132, a second bowtie filter 134, and a third bowtie filter 136. In the illustrated embodiment, the various filters 132, 134, 136 are shown schematically as having different sizes. Alternatively or additionally, for example, the filters 132, 134, 136 may have varying shapes and/or materials. By selecting among the different filters, an X-ray distribution associated with the selected filter may be provided. Discrete bowtie filters may be differently configured for different patient shapes, sizes, or the like. While three discrete filters are shown in FIGS. 1 and 2, other numbers of filters may be employed in various embodiments. The filters may be mounted and used in the system via a carousel, cartridge or the like. The individual filters may be manually placed (e.g., manually placed by an operator receiving a prompt from the processing unit 150 via the display unit 160 to place a particular one of the discrete filters), or may be 45 associated with a mechanism configured to receive a control signal from the processing unit 150 to insert the selected bowtie filter in place for use during performance of an imaging scan.

The adjustable filter module 137 includes a dynamically adjustable bowtie filter 138 shown schematically at a minimum size (shown by solid line) that is adjustable to a maximum size 139 (shown by dashed line). The shape of the dynamically adjustable bowtie filter 138 may also be configurable. The dynamically adjustable bowtie filter 138 may include one or more of mechanical linkages and/or hydraulic actuation mechanisms for adjusting the size and shape of the dynamically adjustable bowtie filter 138. As another example, the dynamically adjustable bowtie filter 138 may include differently sized interchangeable constituent parts that may be variously arranged to provide different sizes and/or shapes. The adjustment of the dynamically adjustable bowtie filter 138 may be adjusted responsive to a control signal received from the processing unit 150. It may be noted that, in some embodiments, the processing unit 150 may select or design a bowtie configuration that either does not yet exist or is not yet available to the adjustable filter module 137 or discrete filter module 131, and the selectable bowtie filter module 130 may include or be associated with a 3-D printing device to produce the configuration not previously available.

As indicated herein, the processing unit 150 is configured to identify an anatomy to be imaged, determine a corresponding image quality and radiation dose for plural bowtie configurations, and select a bowtie configuration based upon the determined corresponding image qualities and radiation doses for the bowtie configurations. For example, the anatomy to be imaged may be identified from an identified protocol or technique entered by an operator and/or using a scout scan. In some embodiments, an operator may identify portions of a scout scan corresponding to the anatomy for which an image is desired. As another example, anatomy recognition software may use identify portions of the scout scan corresponding to an imaging scan to be performed. The corresponding image quality and radiation dose may be determined for all or some available bowtie configurations based on one or more of historical information identifying image quality and radiation dose resulting from use of a same or similar bowtie configuration for a same or similar scan procedure; phantom information providing image quality and radiation dose resulting for phantoms tested with a same or similar bowtie configuration for a same or similar scan procedure; digital simulations of the scan procedure using a same or similar bowtie filter configuration; or analytical relationships describing image quality and/or radiation dosage based on bowtie filter configuration and other scan parameters used as inputs to the analytical relationships.

The depicted processing unit 150 is operably coupled to the input unit 160, the detector 140, and the selectable bowtie filter module 130. The processing unit 150 may include processing circuitry configured to perform one or more tasks, functions, or steps discussed herein. In various embodiments, the processing unit 150 may be configured to obtain a user input corresponding to a scan to be performed (e.g., specifying a clinical mode, scan technique, one or more operational parameters such as tube voltage for performing a scan, or the like), to obtain a position of a patient (e.g., using a scout scan) and to determine a selected bowtie filter configuration for use during performance a scan of the portion, region, or volume to be imaged. The selected bowtie filter configuration, for example, may identify a particular filter to be employed, one or more settings or characteristics of a dynamically adjustable filter, or the like.

In various embodiments, the processing unit 150 may be configured to control one or more aspects of the imaging system 100 to implement a bowtie configuration for a scan to be performed and/or to correct mis-positioning of a patient to be imaged. For example, the processing unit 150 may be operably coupled to the selectable bowtie filter module 130 and configured to provide a control signal to the selectable bowtie filter module 130 to implement the use of a selected bowtie filter configuration. Further, the processing unit 150 may be operably coupled to the cradle 104 and/or the cradle actuation mechanism 106 to adjust the cradle height 105 (e.g., to correct a vertical mis-positioning).

In the illustrated embodiment, the processing unit 150 includes a position module 152, an attenuation module 154, a bowtie selection module 156, and a memory 158. The processing unit 150 may further be configured to control motion of portions of the system, to control the setting of operational scanning parameters used to perform a scan, and/or to reconstruct an image using information from the detector 140 acquired during a scan. It may be noted that other types, numbers, or combinations of modules may be employed in alternate embodiments, and/or various aspects of modules described herein may be utilized in connection with different modules additionally or alternatively.

The depicted position module 152 is configured to identify a position of the object to be positioned, for example to determine if the object if mis-positioned or offset from a center position in one or more directions (e.g., a vertical direction and a lateral direction). In the illustrated embodiment, the position module 152 may be configured to determine positioning using more than one technique.

For example, with reference to FIG. 2, a first technique may be employed to determine if the object 102 is vertically centered. When utilizing the first technique, the position module 152 obtains a scout scan with source 110 positioned to perform a lateral scout scan as seen in FIG. 2 (e.g., with the source 110 positioned at a 9:00 or 3:00 position within the bore of the gantry), and compares a line of maximum attenuation of the scout scan with the center of the scan (where the center of the scout scan corresponds to the center of the field of view, center of bowtie filter, and position of X-ray source). If the line of maximum attenuation and the center of the scout scan (e.g., center of the field of view) are aligned (or within a threshold distance from each other), the object may be understood as vertically aligned. If the line of maximum attenuation and the center of the scout scan or field of view are not aligned (or are beyond a threshold distance from each other), the object 102 may be understood as off-center vertically, or vertically mis-positioned.

A second technique may be used additionally or alternatively to determine centering either laterally or vertically (or other orientation), but will be discussed herein in the context of top-down and/or bottom-up views or azimuths. When utilizing the second technique, the processing unit 150 is configured to determine a cradle height and channel occupancy for the object 102, and to determine the position based on the cradle height and channel occupancy. The channel occupancy may correspond to channels of the detector identified as having an intensity above an intensity threshold, as discussed in connection with FIG. 4. The channel occupancy may be understood as a projection signature corresponding to the projection of the object 102 on the detector 140. By comparing the channel occupancy or projection signature of the object 102 with archived examples of known sizes, shapes, and/or positions at a same or similar cradle height and azimuth, a similar archived size, shape, and position may be used to determine the size, shape, and position of the object 102. For example, the size, shape, and position of the object 102 may be determined or estimated to be the same as the size, shape, and position of the similar archived case, or may be interpolated or estimated between two identified archived cases.

Figure 3:
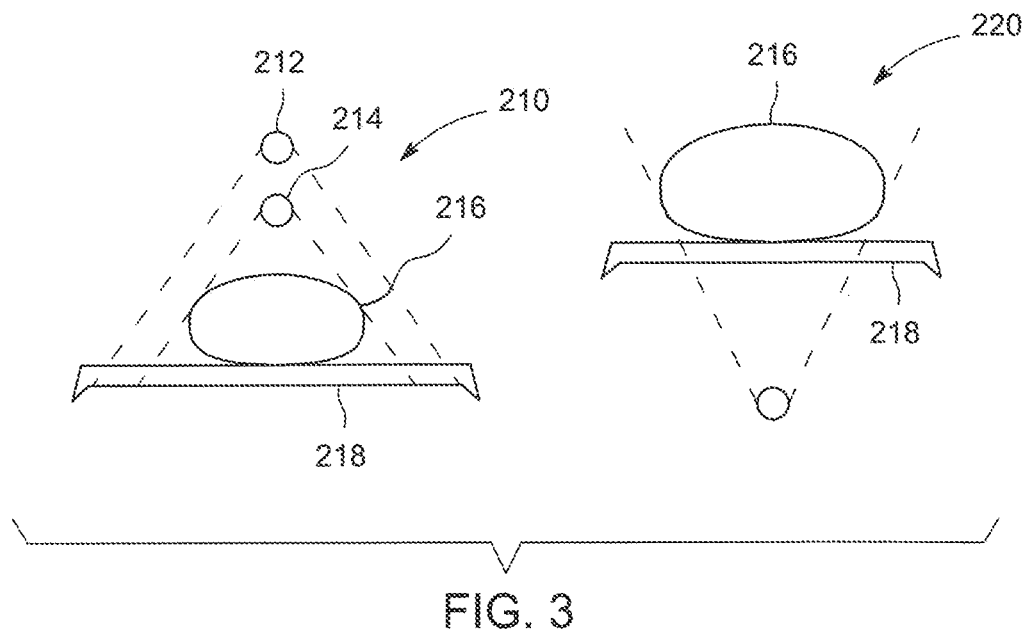
FIG. 3 provides an example of different azimuths.

FIG. 3 illustrates how the position of an object relative to a source (and/or detector) as well as the selected azimuth or view angle may affect a perceived or estimated size of an object. In FIG. 3, an object 216 is shown on a cradle 218. The object 216 is asymmetric vertically. In position 210, two different source locations are shown. A first source location 212 is shown farther from the object 216 than a second source location 214 is shown from the object 216. Because the source locations 212, 214 emit a fan-shaped beam, the object 216 will occupy a larger proportion of the field of view of the second source location 214 than of the field of view of the first source location 212. Thus, the shadow or projection of the object 216 will appear larger to a detector receiving X-rays from the second source location 214 than to a detector receiving X-rays from the first source location 212, even though the object 216 remains the same size. Various embodiments address this potential difficulty by accounting for the distance to the source, for example by considering cradle height. As indicated above, when identifying similar archived cases, the cradle height may be used to interrogate or search an archived library for archived cases measured at a same or similar cradle height, thereby reducing or eliminating the possibility of mis-estimating a size or shape of the object based on variance in distance of the object from an X-ray source.

Similarly, the view or azimuth may affect the apparent size and/or shape of the object. For example, in position 220, the object 216 is viewed from a bottom-up view or azimuth. However, because the object 216 is not vertically symmetric, the apparent size of the object 216 will appear different if viewed from a top-down perspective (e.g., as seen in position 210), even if the distance from the source to the object is the same. Accordingly, in various embodiments, when identifying similar archived cases, the azimuth or view angle may be used to interrogate or search an archived library for archived cases measured at a same or similar azimuth or view angle, thereby reducing or eliminating the possibility of mis-estimating a size or shape of the object based on variance in the azimuth or view angle.

Figure 4:
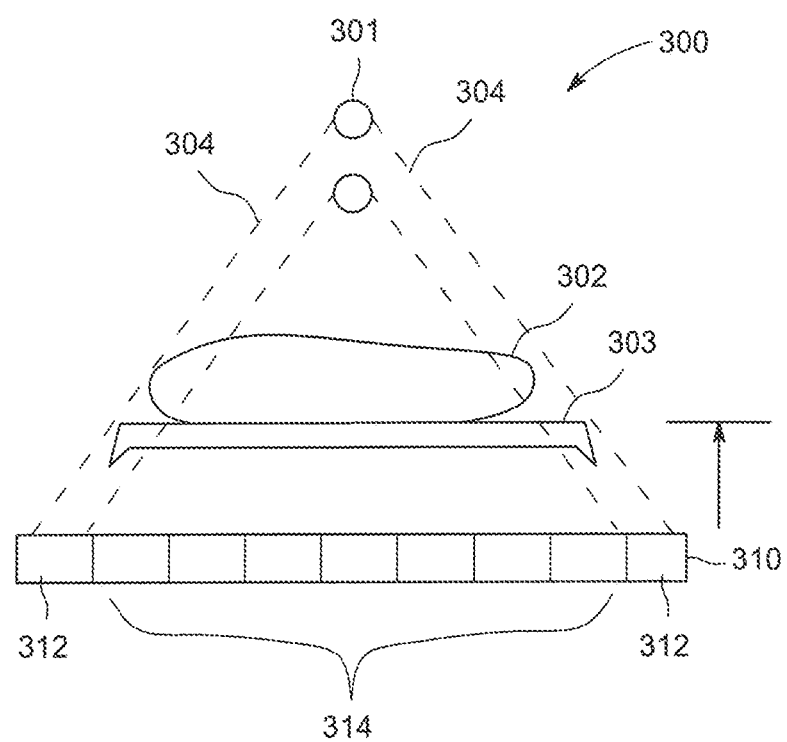
FIG. 4 is a schematic diagram of an imaging system in accordance with an embodiment.

FIG. 4 illustrates a schematic view of a system 300 configured to determine a position and/or attenuation of an object 302 formed in accordance with various embodiments. In FIG. 4, the system 300 includes a cradle 303 upon which the object 302 is supported while X-rays within a field of view 304 from an X-ray source 301 pass through the object 302 to a detector 310. The detector 310 includes channels (which may correspond to pixels) disposed across a width of the detector 310.

In the illustrated embodiment, X-rays passing through the object impinge on an internal group of channels 314, while edge channels 312 receive X-rays directly from the source 301 (e.g., without having passed through the object 302). The intensity signal provided for a given channel may be inversely proportional to the amount of X-rays received, such that the edge channels 312, which receive un-impeded X-rays, may have an intensity at or near zero, with the channels 314, which receive fewer X-rays due to attenuation by the object 302, have a higher intensity than that of the edge channels 312.

For any channel having an intensity above a predetermined threshold, the channel may be determined to be occupied, while channels having an intensity below a threshold may be determined to be unoccupied. Thus, in the illustrated example, the channels 314 may be determined to be occupied while the channels 312 are determined not to be occupied. The channel occupancy may be understood as a projection signature corresponding to the projection of the object 302 on the detector 310. The projection signature in some embodiments may describe which channels are occupied and which are not, without regard to variances in X-rays received due to attenuation above the threshold. In such embodiments, the projection signature or channel occupancy may be understood to describe a width of the object 302. In other embodiments, multiple thresholds corresponding to different attenuation levels may be used to define levels of intensity for the projection signature. For example, for a generally cylindrical object, the intensity levels at the center of the object may vary from the intensities at the edge of the object by a relatively large amount, while for a relatively flat elliptical cross-section the intensity levels at the center of the object may vary from the intensities at the edge of the object by a relatively smaller amount. Thus, the projection signature in some embodiments may convey information regarding a shape of the object 302 as well as a width.

Returning to FIG. 1, the position module 152 may be configured to interrogate a database of known archived sizes, shapes, and positions tabulated or referenced by cradle height and azimuth to identify similar projection signatures at the same or similar cradle height and azimuth. The similar projection signatures may then be used to determine the size, shape, and position of the object to be scanned. For example, the size, shape, and position may be estimated to be the same as the size, shape, and position of the identified archived case. As another example, the size, shape, and position may be interpolated using values for two or more identified similar archived case. For instance, in one example scenario, a profile signature is obtained for an object at a cradle height of X and a top-down (or AP) azimuth. The position module 152 may then search and interrogate a database including projection signatures for objects previously measured at the cradle height of X and top-down azimuth. In the example scenario, the position module 152 may identify a phantom corresponding to a cylinder of 40 centimeters diameter and vertically offset from center by 5 centimeters as having a nearly identical projection signature. The position module 152 may then estimate the object as having a generally cylindrical shape of 40 centimeters in diameter and being offset vertically from center by 5 centimeters. Archived cases may be part of a library of phantom sizes, shapes, and positions corresponding to various cradle heights and azimuths that may be stored in the memory 158 or otherwise accessible to the position module 152. Similarly, archived cases may be a part of a library of cadaver scans and/or historical scans that may be stored in the memory 158 or otherwise accessible to the position module 152.

If the position module 152 (or other aspect of the processing unit 150 determines that the object 102 is not centered (or varies from the center by an amount greater than a threshold), one or more corrective actions may be undertaken. For example, an alert may be provided to a user via the output unit 170. The alert may indicate that the patient is mis-positioned. Further, the alert may indicate an amount and/or direction in which the patient is mis-positioned. Further still, the alert may provide the user with an option to approve a suggested corrected movement. For example, if the patient is determined to be positioned 5 centimeters below center, the user may be provided with an option to approve an upward movement of the cradle 104 of 5 centimeters initiated by the processing unit 150 responsive to approval from the user. As one more example, the processing unit 150 in some embodiments may autonomously adjust the positioning to correct a mis-positioned. Further still, if the patient is not adjusted after a determined mis-positioning, the processing unit 150 may account for the mis-positioning, for example, by selecting a bowtie configuration that will address the mis-positioning, and/or by adjusting one or more scanning parameters. For example, if the mis-positioning is relatively small, the processing unit 150 may increase tube current a relatively small amount to provide additional X-rays to a line of maximum attenuation that is not centered. If the mis-positioning is relatively larger, the processing unit 150 may additionally or alternatively select a bowtie configuration that allows more radiation to pass through to provide still further additional X-rays to a line of maximum attenuation of the object that is further off-center.

The attenuation module 154 is configured to determine an attenuation of the object 102. For example, the determined attenuation may be used in conjunction with automatic exposure control (AEC) mode features or other scanning operating parameters. The attenuation module 154 may use the size, shape, or position determined by the position module 154 using the second technique described above, and estimate the attenuation based on the determined size, shape, or position. In some embodiments, an attenuation value for an identified same or similar archived case may be used as the attenuation estimate.

In other embodiments, an archived cradle-only projection corresponding to the cradle height and azimuth may be identified, and subtracted from the patient scout projection to provide a modified projection. An attenuation estimate may then be generated using conventional methods by summing across all channels of each projection row of the modified projection. Optionally, the attenuation estimation may be normalized or adjusted based on the number of occupied channels in the scout projection.

The bowtie selection module 156 is configured to select a bowtie configuration based on the image quality and/or radiation dosages of various available bowtie configurations for a scan of a given object (e.g., for the given object for a given procedure). For example, the bowtie selection module 156 may obtain one or more of the anatomy to be scanned, the position of the object 102 (e.g., from the position module 152), the attenuation (e.g., from the attenuation module 154), or user inputs corresponding to the scanning technique (e.g., clinical mode, scanning parameters to be used). Using the position (e.g., centered or off-centered), the attenuation, and the scanning techniques, the bowtie selection module 156 may determine corresponding image quality and radiation dosages for available bowtie combinations. The particular metrics used may vary by application, but may include one or more of CNR, total noise, CTDI, SSDE, organ dose, or the like. The image quality and radiation dosages may be estimated using historical information (e.g., case histories of image quality and radiation dosage for similar bowtie configurations used to perform similar scans on similar anatomy), phantom studies (e.g., archived values of image quality and radiation dosage based on data collected for corresponding phantoms at similar bowtie configurations and scanning parameters), digital simulations of scans, or analytic relationships (in tabulated form and/or mathematic expressions) correlating image quality and radiation dosage with bowtie configuration and scanning parameters (e.g., tube voltage, tube current, or the like).

Using the determined image quality metric and/or radiation dosage, the bowtie selection module 156 may identify a bowtie configuration (e.g., a particular discrete bowtie filter or a setting of a dynamically adjustable bowtie filter) that provides a desired or optimal balance between image quality and radiation dosage for a particular patient and/or procedure. The particular relationship, expression, or technique to identify the selected bowtie configuration may vary to suit a given application and/or user. Generally, the relationship or metric used to select the bowtie configuration may be designed or configured to provide a trade-off between image quality and radiation dosage, The particular relationship may be a weighted relationship between image quality and radiation dosage (and/or other parameters). The relationship may be formulaic or tabulated. In some embodiments, one or more image quality metrics may be maximized within a radiation dose constraint, while, in other embodiments, dose may be minimized within an image quality constraint. In various embodiments, different relationships between image quality and radiation dosage for the selected bowtie configuration may vary by scanning procedure (e.g., a first relationship for bone scans, a second relationship for soft tissue scans, or the like). In some embodiments, the bowtie selection module 156 may be configured to present a selected bowtie configuration for approval or denial by a user, while in other embodiments, the bowtie selection module 156 may be configured to autonomously implement the selected bowtie configuration.

The input unit 160 may be configured to obtain an input that corresponds to a clinical mode and/or acquisition parameters or scan technique to be employed for a scan. The input unit 160 may also be configured to obtain user approval or denial of a proposed movement to adjust a position and/or approval or denial of a proposed bowtie configuration. As used herein, to "obtain" may include, for example, to receive. For example, in some embodiments, the input unit 160 may receive an input from a user entered via a touchscreen, keypad, mouse, voice or language recognition device, or the like. Alternatively or additionally, the input unit 160 may receive information from software configured to recognize one or more anatomical structures for example, from a scout image. Accordingly, in some embodiments the input may be a manual input or a user input, while in other embodiments the input may be entered in an automated or semi-automated fashion, for example using an automated or semi-automated segmentation algorithm. Further, in some embodiments, both user and automated inputs may be utilized, and/or a user may be provided with some amount of control or guidance with respect to an otherwise automated input. For example, an input generated automatically (e.g., an anatomy to be scanned identified using an automated algorithm) may be displayed to a user and may be entered subject to user approval and/or modification.

The output unit 170 is configured to provide information to the user. The output unit 170 may be configured to display, for example, a scout image, an alert that a patient is mis-positioned, an amount of mis-positioning, a proposed corrective action, or the like. The output unit 170 may include one or more of a screen, a touchscreen, a printer, or the like.

Figure 5:
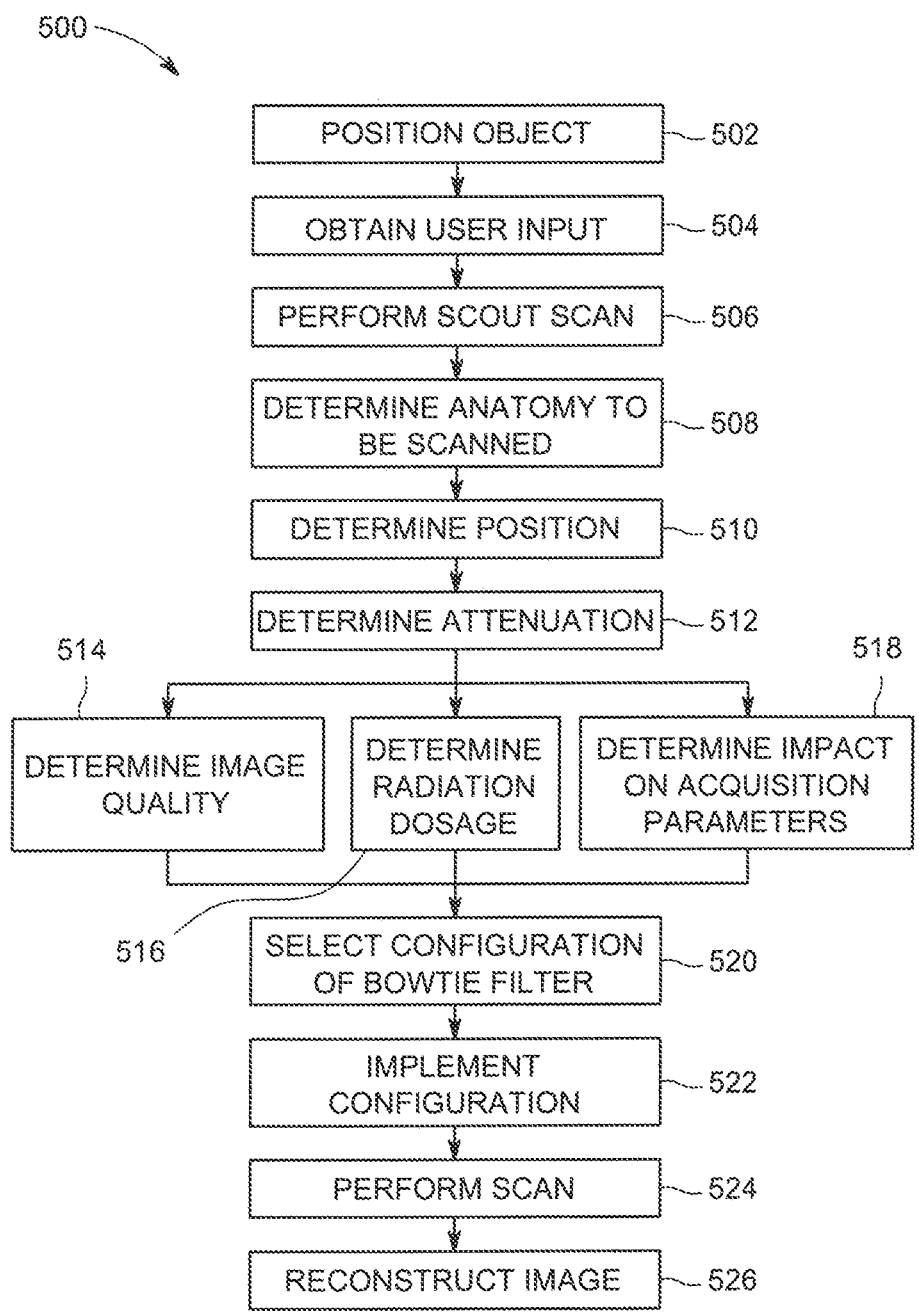
FIG. 5 is a flowchart of a method in accordance with an embodiment.

FIG. 5 provides a flowchart of a method 500 for selecting a bowtie filter configuration for imaging an object (e.g., obtaining a CT image of the object). The method 500, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware (e.g., one or more aspects of the processing unit 150) to perform one or more operations described herein.

At 502, an object to be imaged is positioned. For example, the object may be a human patient positioned on a table (e.g., cradle 104) in the bore of a CT imaging system.

At 504, user input is obtained. For example, the user input may include a scan technique or scanning operational parameters (e.g., tube voltage) and/or a clinical mode (e.g., bone, soft tissue, or the like). The user input may be utilized for example, to determine image qualities and/or radiation dosages for various available or potential bowtie filter configurations.

At 506, a scout scan is performed. The scout scan may be performed, for example, at a dosage level lower than a dosage level used for imaging, and may be performed at a fixed position. In some embodiments, more than one scout scan may be performed, for example at plural positions (e.g., a top-down or bottom-up scan to determine lateral positioning, and a lateral scan to determine vertical positioning).

At 508, anatomy to be scanned is determined. For example, the anatomy to be scanned may be determined using a scout scan. In some embodiments, a user may indicate an area to be scanned on a displayed scout scan (e.g., by marking a desired area to be scanned using a cursor). As another example, anatomical recognition software may be utilized to determine anatomy scanned, for example based on a predetermined protocol or purpose of the scan.

At 510, the position of the object to be scanned is determined, for example, by a processing unit (e.g., processing unit 150). The object may be determined to be centered or off-center in one or more directions relative to the scanning equipment. As one example, a center of a field of view or scout scan may be compared with a line of maximum attenuation to determine if the object is centered vertically. As another example, a projection of the object along with a known cradle height may be used to determine the position (e.g., via comparison with archived case studies correlating projections and cradle heights with sizes, shapes, and/or positions of phantoms or historical case studies). The position may be determined, for example, using one or more aspects of method 600 and/or method 700 discussed herein.

At 512, an attenuation of the object to be imaged is determined. The attenuation may be based on a scout scan, for example, a most recent scout scan obtained if more than one scout scan have been obtained. The determination of attenuation may be performed in conjunction with determining position. The determination of attenuation may be performed, for example, using one or more aspects of method 700 discussed herein. In some embodiments, multiple scout scans may be used together when determining attenuation.

At 514, corresponding image qualities for available or potential bowtie configurations are determined based on anatomy to be scanned, scan technique, clinical mode, position, and/or attenuation. One or more image quality metrics may be obtained, for example corresponding to estimated contrast, noise, or a combination thereof. The particular image quality metric employed may be user-selected or tailored for use by a particular user, or based on user preferences. The particular metric employed may also vary based on procedure (e.g., a first metric for bone scans, a second metric for soft-tissue scans, or the like). The image quality may be determined or estimated, for example, based on historical scans (e.g., historical scans for similar bowtie configurations and scanning parameters), based on phantom studies, based on digital simulations, and/or based on analytical relationships (e.g., using experimentally determined coefficients and/or parameters, curve fitting, or the like).

At 516, corresponding radiation doses for available or potential bowtie configurations are determined based on anatomy to be scanned, scan technique, clinical mode, position, and attenuation. The particular radiation dose metric(s) employed may be user-selected or tailored for use by a particular user, or based on user preferences, and/or may also vary based on procedure (e.g., a first metric for bone scans, a second metric for soft-tissue scans, or the like). The radiation dose may be determined or estimated, for example, based on historical scans, based on phantom studies, based on digital simulations, and/or based on analytical relationships. In various embodiments, after performing steps 514 and 516, each bowtie configuration being considered has associated therewith a particular image quality estimate and a particular radiation dosage estimate corresponding to expected values that would be obtained if the given bowtie configuration were to scan the selected anatomy using the information provided by the user.

At 518, the impact of one or more bowtie configurations on acquisition parameters is assessed. For example, if use of a particular bowtie configuration will require an adjustment to a scanning parameter, such as tube current or voltage, that is outside of a predetermined acceptable range, the bowtie configuration may be rejected or eliminated from further consideration. As another example, bowtie configurations that may be inappropriate for a particular type of scan to be performed (e.g., a pediatric scan may require a particular bowtie filter or not allow one or more other bowtie filters) may be removed from consideration. Bowtie filters to be removed from consideration may be removed from consideration before evaluating image qualities and radiation dosages for bowtie configurations, or may be removed from consideration after evaluating image qualities and radiation dosages.

At 520, a configuration of bowtie filter to be employed for the imaging scan is selected. The configuration may be selected based on the image qualities and radiation dosages determined. In some embodiments, if the final position is an off-centered position, the bowtie filter configuration may be selected to account for the off-centered position (e.g., by providing additional passage of radiation in a portion of the field of view where a line of maximum attenuation is positioned). A bowtie filter configuration providing a best, desired, or optimal combination of image quality and radiation dosage may be selected. In various embodiments, the configuration may be selected, for example, based on a metric that combines image quality and radiation dosage, based on a weighted relationship between image quality and radiation dosage, based on an optimized image quality within a radiation dosage constraint, based on a minimum radiation dosage within an image quality restraint, or the like.

At 522, the selected bowtie filter configuration is implemented. The configuration may be implemented manually, for example by a user placing a bowtie filter selected (e.g., selected by a processing unit such as processing unit 150) in position in an imaging system. The configuration may be implemented automatically, for example by a mechanism controlled by a processing unit. In some embodiments, a user may be provided with a prompt describing the selected configuration and requesting approval to implement the selected configuration. If the user approves (e.g., by making a selection using the input unit 160), the processing system may then send a control signal to the mechanism to place the selected filter in place (or make the necessary adjustments to a dynamically adjustable bowtie filter). In other embodiments, the implementation may be performed autonomously without user intervention, or in some embodiments, without user knowledge of the selected configuration. In some embodiments, for a dynamic bowtie, a bowtie position or configuration for each time during a scan may be determined.

At 524, a scan is performed. The X-ray source and detector may be rotated about the object being imaged and operated in a manner prescribed by predetermined scanning parameters (e.g., operational scanning parameters used to estimate radiation dosage and image quality for the various bowtie filter configurations) to collect imaging information at the detector.

At 526, an image is reconstructed. The image is reconstructed based on imaging information acquired via the detector during an imaging scan.

Figure 6:
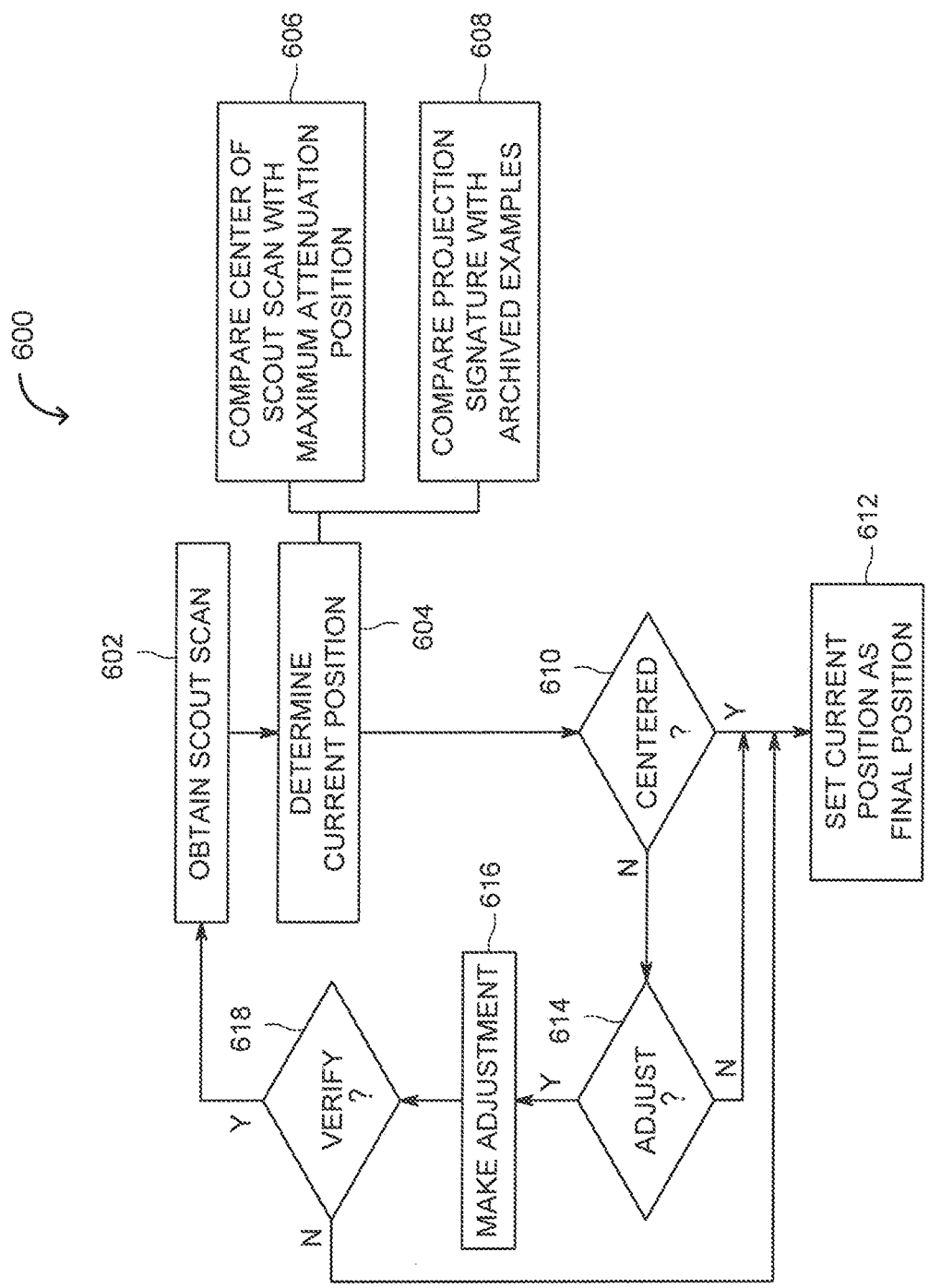
FIG. 6 is a flowchart of a method in accordance with an embodiment.

FIG. 6 provides a flowchart of a method 600 for determining position of an object to be scanned. The method 600, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware (e.g., one or more aspects of the processing unit 150) to perform one or more operations described herein.

At 602, a scout scan is obtained. The scout scan may be obtained similar to the scout scan obtained at 502.

At 604, a current position of the object to be imaged is determined. The current position may be described in terms of one or more directions (e.g., vertical or lateral), and may be described with reference to a center position or a desired position. To determine positions in two or more directions, two or more scout scans may be employed (e.g., one scout scan for each direction). In some embodiments, one or more of substeps 606 or 608 may be performed to determine position. For example, at 606, the center of a scout scan (or center of field of view) may be compared with a line of maximum attenuation in the scout scan. The difference between the center of the scan and the line of maximum attenuation may be understood as an offset from a centered position. As another example, at 608, a projection signature (e.g., at a specified cradle height and azimuth) from the scout scan may be compared with archived cases to identify a similar projection corresponding to a known size, shape, and position of object, and used to determine size, shape, and position of the object to be imaged. In some embodiments, the position may be determined using an analytic relationship between projection signature and position developed using case studies (e.g., at given cradle height and azimuth).

At 610, it is determined if the object to be imaged is centered (e.g., at a centered position or within a threshold distance of the centered position). If the object to be imaged is centered, the method 600 proceeds to 612, and the current position is set as a final position to be used, for example, in determining selected bowtie configuration.

If it is determined that the object to be imaged is not centered, the method proceeds to 614. At 614, it is determined if the position of the object is to be adjusted. For example, in some instances, it may not be desirable or advisable to adjust the position. For example, a patient constraint (such as an injury) may make movement difficult for a patient. If it is determined not to adjust the position, the method 600 proceeds to 612 and the current position is set as the final position. If the final position is an off-centered position, the off-centered position may be recorded and later utilized to determine or adjust the particular bowtie configuration selected. For example, to account for an off-centered position, a bowtie configuration and/or scanning parameters may be selected to increase the amount of X-rays allowed to pass to a line of maximum attenuation that is off-centered.

If the position is to be adjusted, the method 600 proceed to 616, and the position is adjusted. For example, a patient may be moved laterally on a cradle or table. As another example, the cradle may be raised or lowered an amount to account for the determined off-center position. In various embodiments, the cradle may be adjusted automatically or manually.

At 618, it is determined if the adjustment to position is to be verified. For example, if the adjustment to position is made automatically and/or there is a high degree of confidence that the adjustment resulted in a centered position, an additional scout scan to verify position may not be desired. If position is not to be verified, the current position may be understood as centered and the method 600 may proceed to 612. If the position is to be verified, the method 600 may proceed to 602 and a new scout scan may be obtained for the newly adjusted position.

Figure 7:
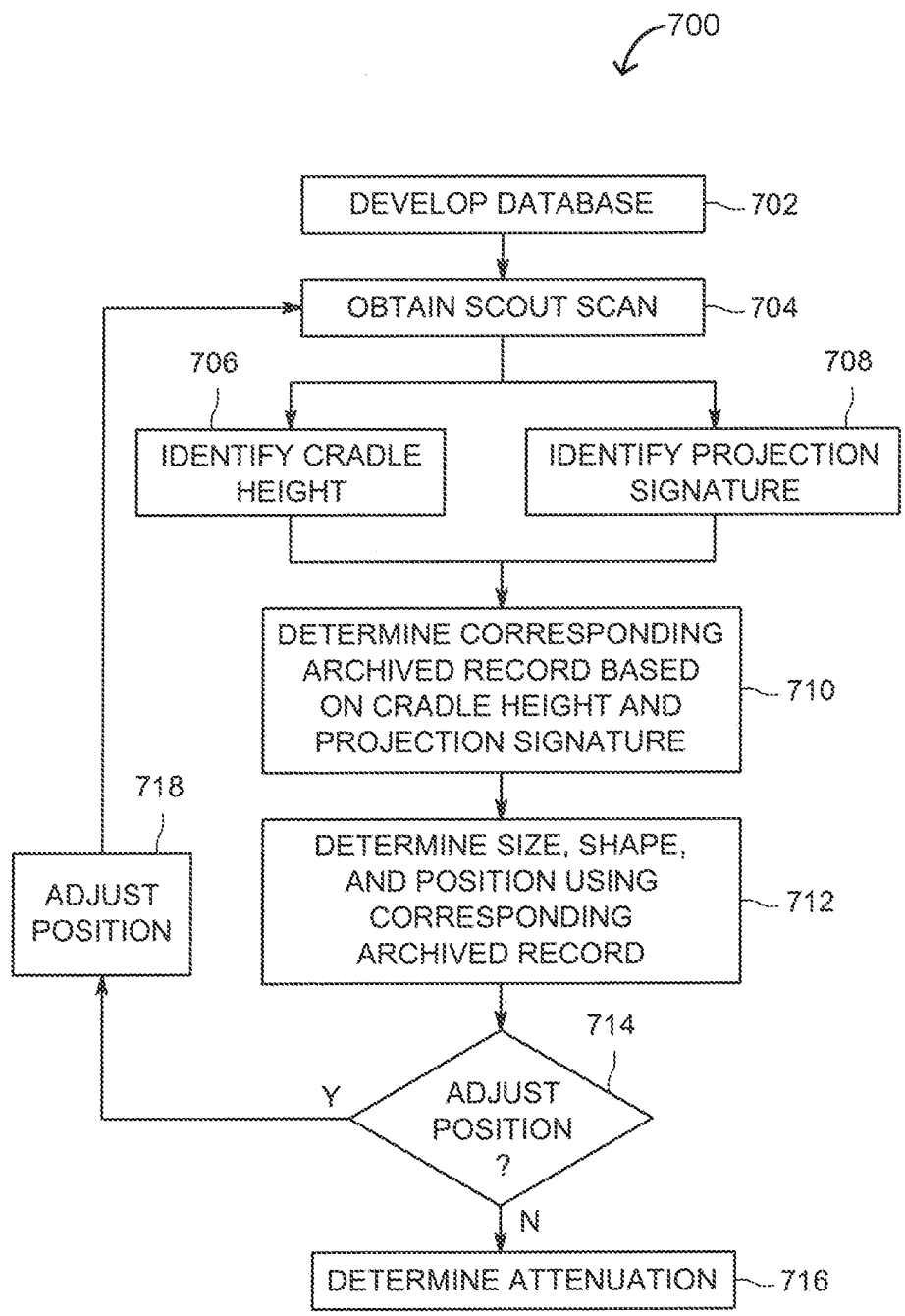
FIG. 7 is a flowchart of a method in accordance with an embodiment.

FIG. 7 provides a flowchart of a method 700 for determining position and/or attenuation of an object to be scanned. The method 700, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the processing unit 150) to perform one or more operations described herein.

At 702 a database describing sizes, shapes, and/or positions of phantoms, cadavers, and/or historical case studies corresponding to, for example cradle height, azimuth, and projection signature combinations is developed. The database may contain a relatively large number of entries in some embodiments including various sizes and shapes at numerous cradle heights as well centered and off/centered positions. In other embodiments, the database may contain a smaller number of entries which may be used to derive or develop formulaic or tabulated relationships between size, shape, and position with cradle height, azimuth, and projection signature combinations. The database may also include cradle only projections for various cradle heights and azimuths or view angles, which may be used to correct for the presence of the cradle when determining attenuation characteristics of an object to be imaged.

At 704, a scout scan is obtained. The azimuth or view angle of the scout scan may be determined and recorded for later use, for example in interrogating a database to identified archived cases recorded using the same azimuth or view angle.

At 706, the cradle height for the object during the scout scan is identified. For example, a positional sensor may provide information describing the cradle height or position. As another example, a cradle actuation mechanism may provide information describing the cradle height, for example information describing a setting of the cradle actuation mechanism corresponding to a particular cradle position or height.

At 708, a projection signature for the scout scan is identified. The projection signature, for example, may identify all detector channels having an intensity above a threshold level. In some embodiments, relative levels of intensity for detector channels may be included in the projection signature.

At 710, a corresponding archived record is determined for the object based on the cradle height and projection signature. For example, archived cases (of phantoms, cadavers, and/or historical case studies) may identify sizes, shapes, and/or positions corresponding to cradle height and projection signature combinations. Analytical relationships (e.g., interpolations between archived values, mathematical or tabulated relationships extrapolated or determined from archived case studies, for example via curve fitting) may be employed alternatively or additionally to determine size, shape and position.

At 712, the size, shape, and/or position of the object are determined, based on the corresponding archived record. For example, the size, shape, and/or position of the object to be imaged may be estimated as the size, shape and/or position of the archived record, and/or interpolated between two or more archived records (e.g., archived records having similar projection signatures, similar cradle heights, and/or similar azimuths).

At 714, it is determined if the position is to be adjusted. If the position is not to be adjusted, the method 700 proceeds to 716. At 716, the attenuation is determined. In some embodiments, the attenuation of the object may be estimated as being similar to the attenuation of a similar archived record (e.g., a historical case study having a similar size, shape, position, cradle height, and azimuth). In some embodiments, scout projection information may be adjusted to account for the cradle (e.g., a cradle only projection at the same cradle height as the scout scan may be subtracted or removed from the scout projection to provide modified projection information) and patient attenuation may be determined, for example, based on the modified projection information using conventional techniques. The patient attenuation estimation in various embodiments may be normalized or adjusted based on occupied channels.

If the position is to be adjusted, the method 700 proceeds to 718 and the position is adjusted. After the position is adjusted, the method 700 may proceed to 702, with a new scout scan obtained at the newly adjusted position.

Various embodiments discussed or described herein provide for improved selection or determination of bowtie filter configurations. Additionally or alternatively, various embodiments provide for improved position identification and/or correction of mis-positioned patients. Various embodiments also address one or more criteria (e.g., image quality, radiation dosage) in the determination of a bowtie filter configuration.

Figure 8:
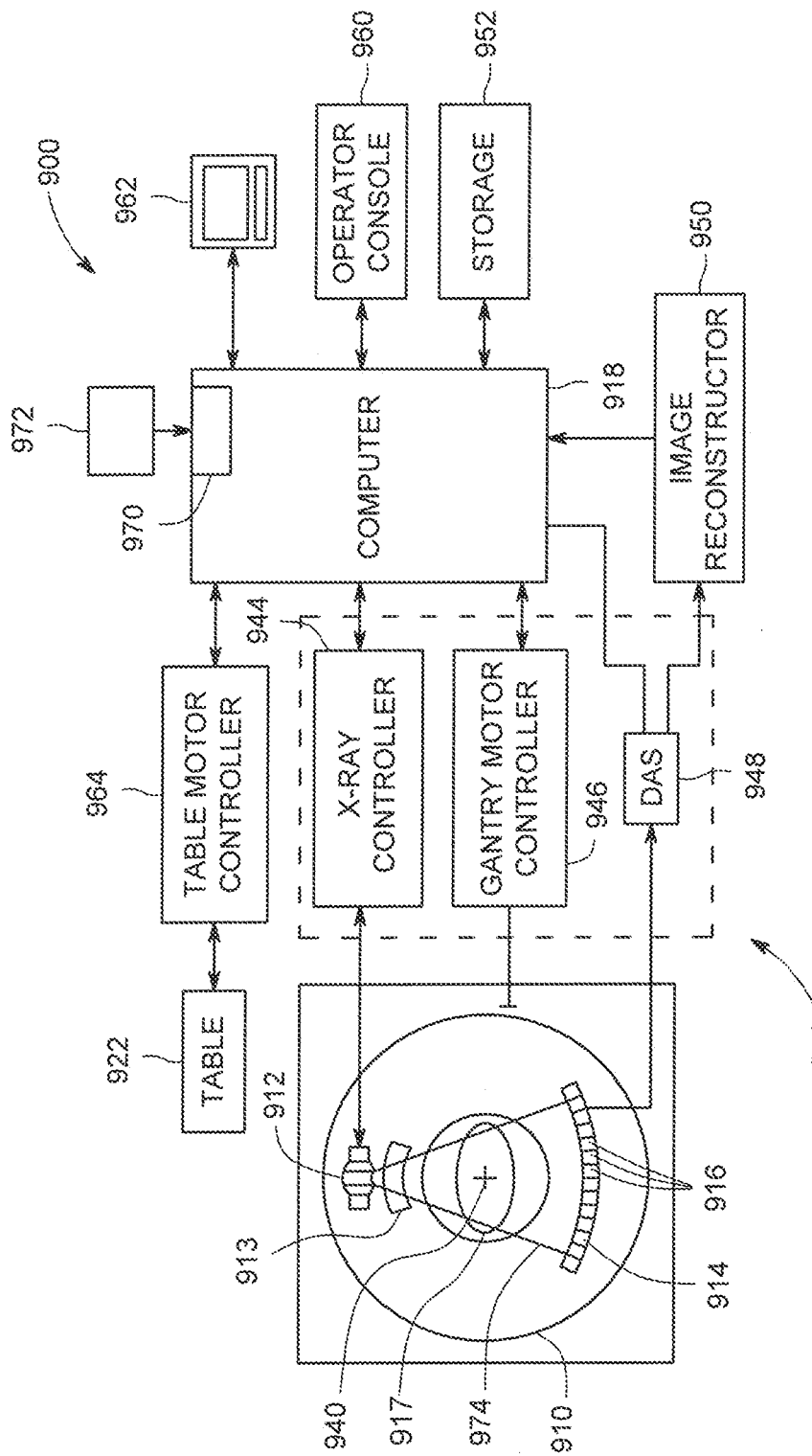
FIG. 8 is a schematic block diagram of a computed tomography (CT) imaging system in accordance with an embodiment.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be realized that the CT imaging system 900 may form part of a multi-modality imaging system. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module (not shown in FIG. 8, see, e.g., selectable bowtie filter module 130) are provided proximate the X-ray source 912. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910

As discussed above, the detector 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 150 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view". A "scan" of the subject 917 comprises a set of views made at different gantry angles, or view angles, during one or more revolutions of the X-ray source 912 and the detector 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A computed tomography (CT) imaging system comprising:
    a selectable pre-object filter module interposed between an X-ray source and an object to be imaged, the selectable pre-object filter module configured to absorb radiation from the X-ray source to control distribution of X-rays passed to the object to be imaged, the selectable pre-object filter module comprising plural pre-object filter configurations providing corresponding X-ray distributions, wherein the selectable pre-object filter module is selectable between the plural configurations to provide a selected pre-object filter configuration of the plural pre-object filter configurations to perform a desired imaging scan of the object to be imaged;
    a detector configured to receive X-rays that have passed through the object to be imaged; and
    a processing unit operably coupled to the selectable pre-object filter module and the detector, the processing unit configured to:
        identify an anatomy to be imaged;
        determine a corresponding image quality metric and radiation dose metric separately for each of the plural pre-object filter configurations based on particular operational parameters to be used to perform the desired imaging scan, wherein the operational parameters include tube voltage and tube current; and
        select the selected pre-object filter configuration from among the pre-object filter configurations based upon the separately determined corresponding image quality metrics and radiation dose metrics.

2. The imaging system of claim 1, wherein the processing unit is further configured to implement the selected pre-object filter configuration for use in performing the desired imaging scan of the object to be imaged.

3. The imaging system of claim 1, wherein the selectable pre-object filter module comprises a plurality of discrete bowtie filters, wherein the processing unit is configured to select one of the discrete bowtie filters for use in performing the desired imaging scan of the object to be imaged.

4. The imaging system of claim 1, wherein the selectable pre-object filter module comprises a dynamically adjustable bowtie filter, wherein the processing unit is configured to adjust the dynamically adjustable bowtie filter to provide the selected bowtie configuration.

5. The imaging system of claim 1, wherein the processing unit is further configured to obtain a pre-scan, and determine a position of the object relative to a centered position using the pre-scan.

6. The imaging system of claim 5, wherein the processing unit is further configured to alert a user if the position of the object differs from the centered position by more than a threshold.

7. The imaging system of claim 5, wherein the processing unit is further configured to adjust a cradle position of a cradle upon which the object to be imaged is supported if the position of the object differs from the centered position by more than a threshold.

8. The imaging system of claim 5, wherein the processing unit is configured to determine a cradle position and channel occupancy for the object to be imaged, the channel occupancy corresponding to channels of the detector having a signal metric above a threshold, and to determine the position based on the cradle position and channel occupancy.

9. The imaging system of claim 1, wherein the processing unit is configured to determine a cradle position and channel occupancy for the object to be imaged, the channel occupancy corresponding to channels of the detector having a signal metric above a threshold, and to determine an attenuation for the object to be imaged based on the cradle position and channel occupancy.

10. A method comprising:
identifying, with at least one processing unit, an anatomy to be scanned for a desired imaging scan by a computed tomography (CT) imaging system including a selectable pre-object filter module having plural pre-object filter configurations providing corresponding X-ray distributions;
determining, with the at least one processing unit, a corresponding image quality metric separately for each of the plural pre-object filter configurations based on particular operational parameters to be used to perform the desired imaging scan, wherein the operational parameters include tube voltage and tube current;
determining, with the at least one processing unit, a corresponding radiation dosage metric separately for each of the plural pre-object filter configurations based on operational parameters; and
selecting, with the at least one processing unit, a selected pre-object filter configuration for performing the desired imaging scan of the anatomy to be scanned from among the plural pre-object filter configurations based upon the separately determined corresponding image quality metrics and radiation dosage metrics.

11. The method of claim 10, further comprising automatically implementing the selected pre-object filter configuration and performing the desired imaging scan using the selected pre-object filter configuration.

12. The method of claim 10, wherein the plural pre-object filter configurations correspond to a corresponding plurality of discrete bowtie filters, and wherein the selecting comprises selecting one of the discrete bowtie filters for performing the desired imaging scan.

13. The method of claim 10, further comprising obtaining a pre-scan, and determining, with the at least one processing unit, a position of an object to be imaged relative to a centered position using the pre-scan.

14. The method of claim 13, further comprising alerting a user if the position of the object differs from the centered position by more than a threshold.

15. The method of claim 13, further comprising adjusting a cradle dimension of a cradle upon which the object to be imaged is supported if the position of the object differs from the centered position by more than a threshold.

16. The method of claim 13, further comprising:
determining, with the at least one processing unit, a cradle position and channel occupancy for the object to be imaged, the channel occupancy corresponding to channels of a detector having a signal metric above a threshold; and
determining, with the at least one processing unit, the position based on the cradle position and channel occupancy.

17. The method of claim 10, further comprising:
determining a cradle position and channel occupancy for the object to be imaged, the channel occupancy corresponding to channels of a detector having a signal metric above a threshold; and
determining an attenuation for the object to be imaged based on the cradle position and channel occupancy.

18. A tangible and non-transitory computer readable medium configured to select a pre-object filter configuration for an object to be imaged, the tangible and non-transitory computer readable medium comprising one or more computer software modules configured to direct one or more processors to:
identify an anatomy to be scanned for a desired imaging scan by a computed tomography (CT) imaging system including a selectable pre-object filter module having plural pre-object filter configurations providing corresponding X-ray distributions;
determine a corresponding image quality metric separately for each of the plural pre-object filter configurations based on particular operational parameters to be used to perform the desired imaging scan, wherein the operational parameters include tube voltage and tube current;
determine a corresponding radiation dosage metric separately for each of the plural pre-object filter configurations based on the operational parameters; and
select a selected pre-object filter configuration from among the plural pre-object filter configurations for performing the desired imaging scan of the anatomy to be scanned based upon the separately determined corresponding image quality metrics and radiation dosage metrics.

19. The tangible and non-transitory computer readable medium of claim 18, wherein the computer readable medium is further configured to direct the one or more processors to obtain a pre-scan, and determine a position of an object to be imaged relative to a centered position using the pre-scan.

20. The tangible and non-transitory computer readable medium of claim 18, wherein the computer readable medium is further configured to direct the one or more processors to
determine a cradle position and channel occupancy for the object to be imaged, the channel occupancy corresponding to channels of a detector having a signal metric above a threshold; and
determine an attenuation for the object to be imaged based on the cradle position and channel occupancy.

21. The imaging system of claim 1, wherein the processing unit is further configured to select the selected pre-object filter configuration based on an impact of at least one of the pre-object filter configurations on acquisition parameters.

22. The imaging system of claim 1, wherein the processing unit is further configured to remove an inappropriate pre-object filter configuration when use of the inappropriate pre-object filter configuration requires adjustment of at least one of a tube current or voltage outside of a predetermined acceptable range.

* * * * *